(12) United States Patent  
Boeke et al.

(10) Patent No.: US 9,140,666 B2  
(45) Date of Patent: Sep. 22, 2015

(54) CAPILLARY ELECTROPHORESIS SYSTEM

(75) Inventors: Bruce R. Boeke, Ames, IA (US); Martin Chris Foster, Nevada, IA (US); Thomas J. Kurt, Ames, IA (US); Scott Stueckradt, Huxley, IA (US)

(73) Assignee: Advanced Analytical Technologies, Inc., Ames, IA (US)

( * ) Notice: Subject to any disclaimer, the term of this patent is extended or adjusted under 35 U.S.C. 154(b) by 246 days.

(21) Appl. No.: 13/470,870

(22) Filed: May 14, 2012

(65) Prior Publication Data

US 2013/0292250 A1   Nov. 7, 2013

Related U.S. Application Data

(63) Continuation-in-part of application No. 29/421,549, filed on Mar. 15, 2012, now Pat. No. Des. 689,621.

(60) Provisional application No. 61/643,411, filed on May 7, 2012.

(51) Int. Cl.  
*G01N 27/447* (2006.01)

(52) U.S. Cl.  
CPC ............................ *G01N 27/44743* (2013.01)

(58) Field of Classification Search  
CPC ........... G01N 27/447; G01N 27/44743; B01L 2400/0415; B01L 2400/0421; C07K 1/28; B01D 57/02

USPC ................ 204/450–470, 546–550, 600–621, 204/641–645

See application file for complete search history.

(56) References Cited

U.S. PATENT DOCUMENTS

| 5,324,401 | A | 6/1994 | Yeung et al. |
|---|---|---|---|
| 5,695,626 | A * | 12/1997 | Yeung et al. ................... 204/605 |
| 6,828,567 | B2 | 12/2004 | Amirkhanian et al. |
| 6,833,062 | B2 | 12/2004 | Kennedy et al. |
| 7,118,659 | B2 | 10/2006 | Kurt et al. |
| 8,216,512 | B2 * | 7/2012 | Winther et al. ................. 422/67 |
| 2002/0108857 | A1 * | 8/2002 | Paschetto et al. ............. 204/457 |
| 2010/0126857 | A1 | 5/2010 | Polwart et al. |

OTHER PUBLICATIONS

Applied Biosystems—by Life Technologies, http://www6.appliedbiosystems.com/products/abi3730xlspecs.cfm [retrieved from the Internet on Feb. 24, 2014] pp. 2-5.

* cited by examiner

*Primary Examiner* — J. Christopher Ball  
*Assistant Examiner* — Maris R Kessel  
(74) *Attorney, Agent, or Firm* — McKee, Voorhees & Sease, PLC

(57) ABSTRACT

The invention is an improved multiplex capillary electrophoresis instrument or module with at least four and preferably six user-accessible vertically stacked drawers. An x-z stage moves samples from the user accessible drawers to the capillary array for analysis. A computer program allows users to add capillary electrophoresis jobs to a queue corresponding to the analysis of rows or plates of samples without stopping or interrupting runs in progress.

10 Claims, 15 Drawing Sheets

CAPILLARY ELECTROPHORESIS SYSTEM

CROSS-REFERENCE TO RELATED APPLICATIONS

This application is a continuation in part of commonly owned co-pending earlier filed design case, U.S. Ser. No. 29/421,549 filed Mar. 15, 2012, and claims priority of earlier filed provisional application U.S. Ser. No. 61/643,411 filed May 7, 2012, which applications are hereby incorporated by reference in their entirety.

BACKGROUND OF THE INVENTION

1. Field of the Invention

This invention relates to a system and software for multichannel capillary electrophoresis.

2. Description of Related Art

The current next-generation sequencing (NGS) platforms use a variety of technologies for sequencing, including pyrosequencing, ion-sequencing, sequencing by synthesis, or sequencing by ligation. Although these technologies have some minor variations, they all have a generally common DNA library preparation procedure, which includes genomic DNA quality & quality assessment, DNA fragmentation and sizing (involving mechanical shearing, sonication, nebulization, or enzyme digestion), DNA repair and end polishing, and a last step of platform-specific adaptor ligation. With a rapidly growing demand for DNA sequence information, there is a critical need to reduce the time required for the preparation of DNA libraries.

A labor-intensive step in DNA library preparation is the qualification (size determination) and quantification of both un-sheared genomic DNA and downstream fragmented DNA. Existing methods for DNA fragment analysis include agarose gel electrophoresis, capillary electrophoresis, and chip-based electrophoresis. Agarose gel electrophoresis is labor intensive, requiring gel preparation, sample transfer via pipetting, and image analysis. The images obtained by agarose electrophoresis are often distorted, resulting in questionable or unreliable data. It is impossible to use agarose gel electrophoresis for accurate quantification of DNA, which means that a separate, second method (UV or fluorescence spectroscopy) is required for quantification. Finally, agarose gel electrophoresis is difficult to automate. Chip or microchip based electrophoresis provides an improvement in data quality over agarose gel electrophoresis but is still labor intensive. For example, chip-based methods require manual steps to load gel, markers and samples. Even though these microchip or chip based electrophoresis units can run a single sample in seconds or minutes, the sample and gel loading are barriers to ease-of-use, especially when running hundreds or thousands of samples. Also, existing chip-based systems are unable to quantify genomic DNA. Capillary electrophoresis (CE) offers advantages over both agarose electrophoresis and microchip electrophoresis in that gel-fill and sample loading is automated.

Multiplex capillary electrophoresis is known. For example Kennedy and Kurt in U.S. Pat. No. 6,833,062 describe a multiplex absorbance based capillary electrophoresis system and method. Yeung et al. in U.S. Pat. No. 5,324,401 describe a multiplex fluorescent based capillary electrophoresis system. Although these systems offer the advantage of analyzing multiple samples simultaneously, and can run several plates sequentially, they lack the ability to load or change multiple sample plates while the system is running, and they also lack a simple workflow for efficient sample analysis.

While existing commercial CE systems can be automated with a robotic system, stand-alone systems are not fully automated or lack the sensitivity and data quality required for adequate DNA library analysis. An example of a CE instrument with a robot-capable interface is given by Kurt et al. in U.S. Pat. No. 7,118,659. For the construction of DNA libraries, as well as other applications such as mutation detection, it is often necessary to run thousands of samples per day, but the implementation of a robotic system for sample handling is prohibitively expensive, and many labs lack the expertise necessary for the maintenance and operation of sophisticated robotic systems. Automated forms of micro-slab-gel electrophoresis have been developed, such as those described in United States Patent Application number 20100126857. These allow for automatic analysis of multiple samples, but the techniques either still require significant human intervention, or they do not have the throughput required for high-volume applications. Amirkhanian et al. in U.S. Pat. No. 6,828,567 describe a 12-channel multiplex capillary electrophoresis system capable of measuring up 12 samples at a time using multiplex capillary electrophoresis. However, this system is not capable of measuring multiple 96-well plates, and does not have the workflow that allows the analysis of thousands of samples per day.

As can be seen, there a need for an automated capillary electrophoresis system that a) eliminates the complexity, cost, and required expertise of a robotic system b) enables users to run from one to several thousand samples per day and c) allows users to conveniently load several plates or samples onto a capillary electrophoresis system while the system is running other samples and d) has the small size and footprint of a stand-alone capillary electrophoresis unit.

This invention has as a primary objective the fulfillment of the above described needs.

BRIEF SUMMARY OF THE INVENTION

The present invention is a multiplex capillary electrophoresis system and console with an improved sample handling and control method for the analysis of samples.

One embodiment of the invention is a console with a series of at least four and preferably at least six vertically stacked user-accessible drawers that can each hold a plate containing from 1 to 384 sample wells. Preferably, each user accessible drawer holds a sample plate containing 96 sample wells. The system is configured so that sample plates can be loaded onto the system at any time, including during the electrophoresis or analysis of samples. User "A" can walk up to the machine, load a row of 12 samples, enter loading and analysis instructions onto the computer and walk away. While user "A" samples are running, user "B" can walk up to the machine, load a tray of 96 samples, enter loading and analysis instructions and walk away. User "C" can walk up to the machine, load 12 samples, while either user "A" or user "B" samples are running, enter loading and analysis instructions, and walk away. Two of the preferred six user-accessible drawers are used to hold an electrophoresis run buffer and a waste tray.

Another embodiment of the invention is a mechanical stage that transports sample trays and/or buffer or waste trays from any one of the vertically stacked user-accessible drawers to the injection electrodes and capillary tips of the multiplex capillary array of the capillary electrophoresis subsystem.

Another embodiment of the invention is uses a computer program that enables a user to create a queue of jobs, with each job representing an analysis of a new set of samples. This computer system enables users to enter job data even when the system is running samples. For example, user "A" loads "sample plate 1" into the system into Drawer 3 and uses a computer program to add a job to a queue, the job representing the injection and capillary electrophoresis of samples in "sample plate 1" in Drawer 3. While the system is running user A's samples, user B loads plate 2 into Drawer 4 and uses the same computer program to add a job to a queue, the job representing the injection and capillary electrophoresis of samples in "sample plate 2" in Drawer 4. User C loads "sample plate 3" into Drawer 5 and uses the same computer program to add a job to the queue, the job representing the injection and capillary electrophoresis of samples in "sample plate 3" in Drawer 5.

A preferred embodiment of this invention is a system capable of allowing the user to enter 24 or more individual jobs to a queue, with each job representing an injection and analysis of a plurality of samples.

An even more preferred embodiment is a system capable of allowing the user to enter 48 or more individual jobs to a queue, with each job representing an injection and analysis of a plurality of samples.

Another embodiment is a system capable of allowing the user to enter 100 or more individual jobs to a queue, with each job representing an injection and analysis of a plurality of samples.

DETAILED DESCRIPTION OF THE INVENTION

The invention is a multiplexed capillary electrophoresis system with enhanced workflow. The capillary electrophoresis system and apparatus of the present invention includes an absorbance or fluorescence-based capillary electrophoresis sub-system with a light source, a method for carrying light from the light source to the sample windows of a multiplex capillary array containing at least 12 capillaries (preferably 96 capillaries), and a method for detecting light emitted (fluorescence) or absorbed (absorbance) from the sample windows of a multiplex array. The sub-system also includes a method for pumping buffers and gels through the capillaries, as well as a method for application of an electric field for electrophoretic separation. The optics of the fluorescent-based sub system of the present invention are described by Pang in United States Patent Applications 20070131870 and 20100140505, herein incorporated by reference in their entirety. The optics of an applicable absorbance-based system, as well as the fluid handling, reservoir venting, application of electric field, and selection of fluids via a syringe pump and a 6-way distribution valve are discussed by Kennedy et al. in U.S. Pat. Nos. 7,534,335 and 6,833,062, herein incorporated by reference their entirety.

Figure 1:
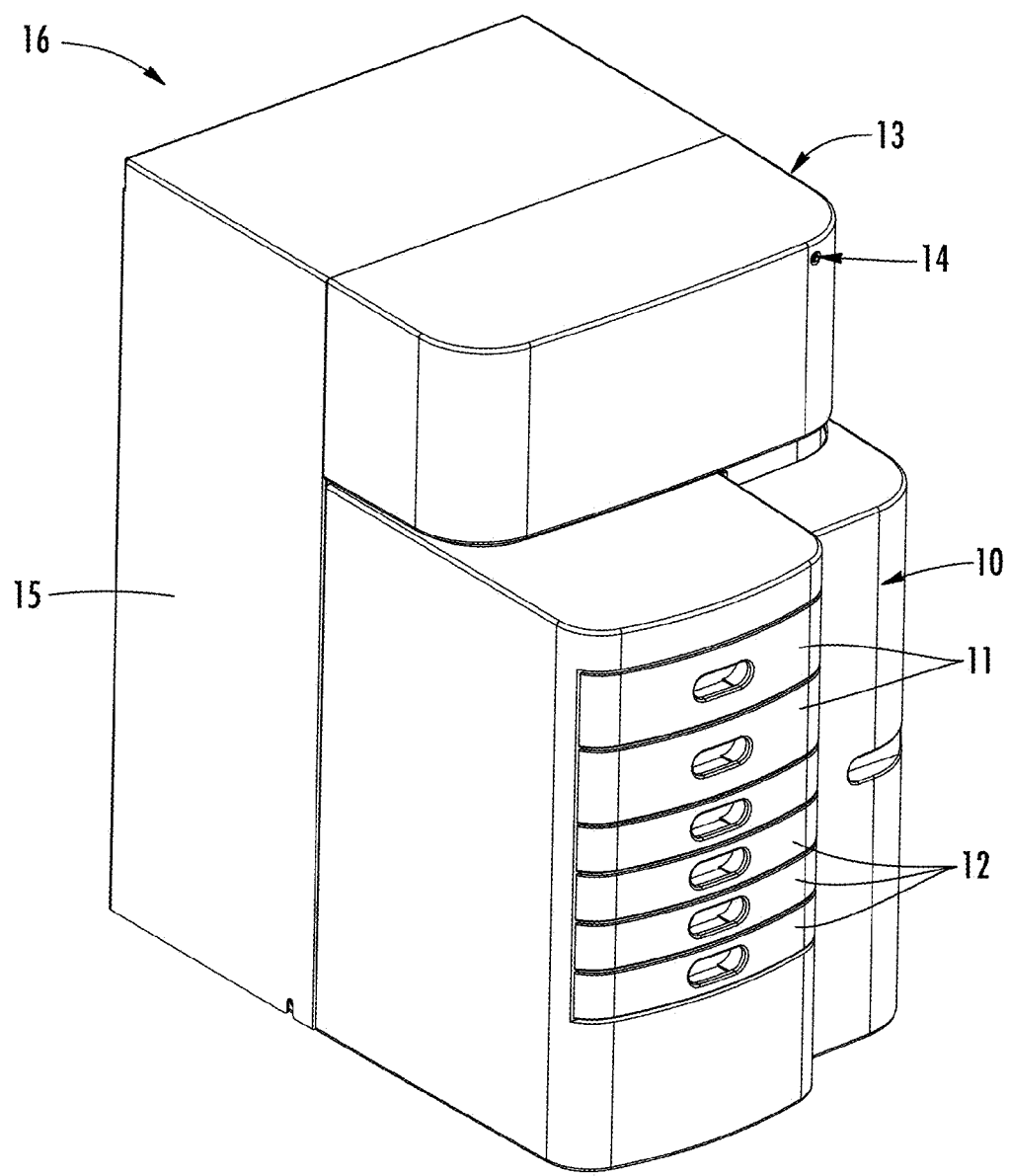
FIG. 1 shows a left-front-view of the instrument, with 6 drawers for holding sample and buffer plates.

Referring to FIG. 1 the multiplex capillary system and/or console 16, with enhanced workflow has a door 10 for easy access to the loading of gels, two drawers 11 for the easy loading of a buffer tray and a waste tray. Drawers 12 can be opened for easy loading of 96-well PCR plates, tube strips, vials, or other sample containers. A top door 13 can be opened to access a replaceable capillary array, array window, and reservoir. An indicator light 14 is used to for notifying users of the active application of a high-voltage for electrophoresis. A removable back-panel 15 allows access to electronics such as a high-voltage power supply, electrical communication panels, a pump board, pressure transducer board, and stage driver electronics. The back panel 15 also allows maintenance access to the x-z stage, which is used to move sample trays from the drawers 11 and 12 to a capillary array.

Figure 2:
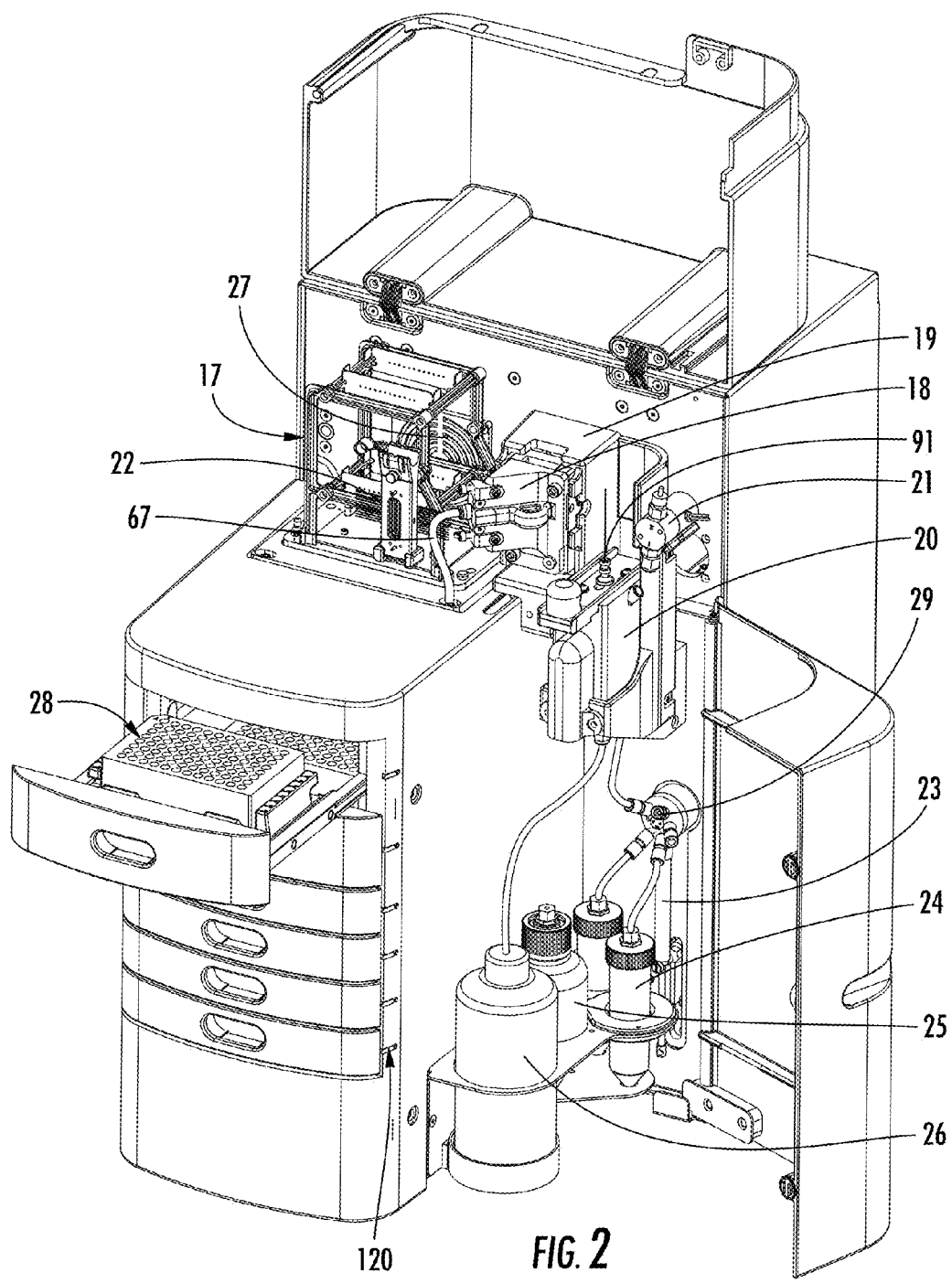
FIG. 2 shows a right-front view of the instrument with one drawer pulled out for placement of a buffer plate and the top and side door compartments open.

FIG. 2 shows the multiplex capillary system used with the enhanced workflow console 16 with the top and side doors open. A replaceable capillary array 17 holds either 12 or 96 capillaries for multiplex capillary electrophoresis. An LED light guide 67 guides light from a LED engine located in the back compartment to the array window block 22 which is inserted between the array window holder 19 and LED light guide and window holder 18. In this view, array window block 22 is attached to the capillary array 17 for display. When the capillary array is removed, from the system, the array window block 22 can be attached to the capillary array 17 (as shown). When the capillary array is fully installed, the array window block 22 is not visible because it is sandwiched between the array window holder 19 and LED light guide and window holder 18. A vent valve 21 is connected to the top of a capillary reservoir 20. A syringe pump 23 coupled with a 6-way distribution valve 29 delivers fluids and electrophoresis gels from fluid containers 24 and 25 into the capillary reservoir 20, waste container 26, or capillaries in the capillary array 17. A fan 27 is used for forcing cool air from the back compartment through the capillary array 17, past the outside of the reservoir 20, down past the fluid containers 24, 25 and finally out the bottom of the instrument. LED indicator lights 120 are used to indicate the presence or absence of trays in the drawers. A buffer tray 28 is shown in a drawer (11, FIG. 1). The capillary array reservoir tip 91 is shown inserted into the reservoir 20.

The concepts and practical implementation of motion control systems are known. For example, Sabonovic and Ohnishi; "Motion Control" John Wiley and Sons, 2011, herein incorporated by reference in its entirety, discusses practical methods for the design and implementation of motion control. It does not, however, show an enhanced CE workflow console 16 as depicted here.

Figure 3:
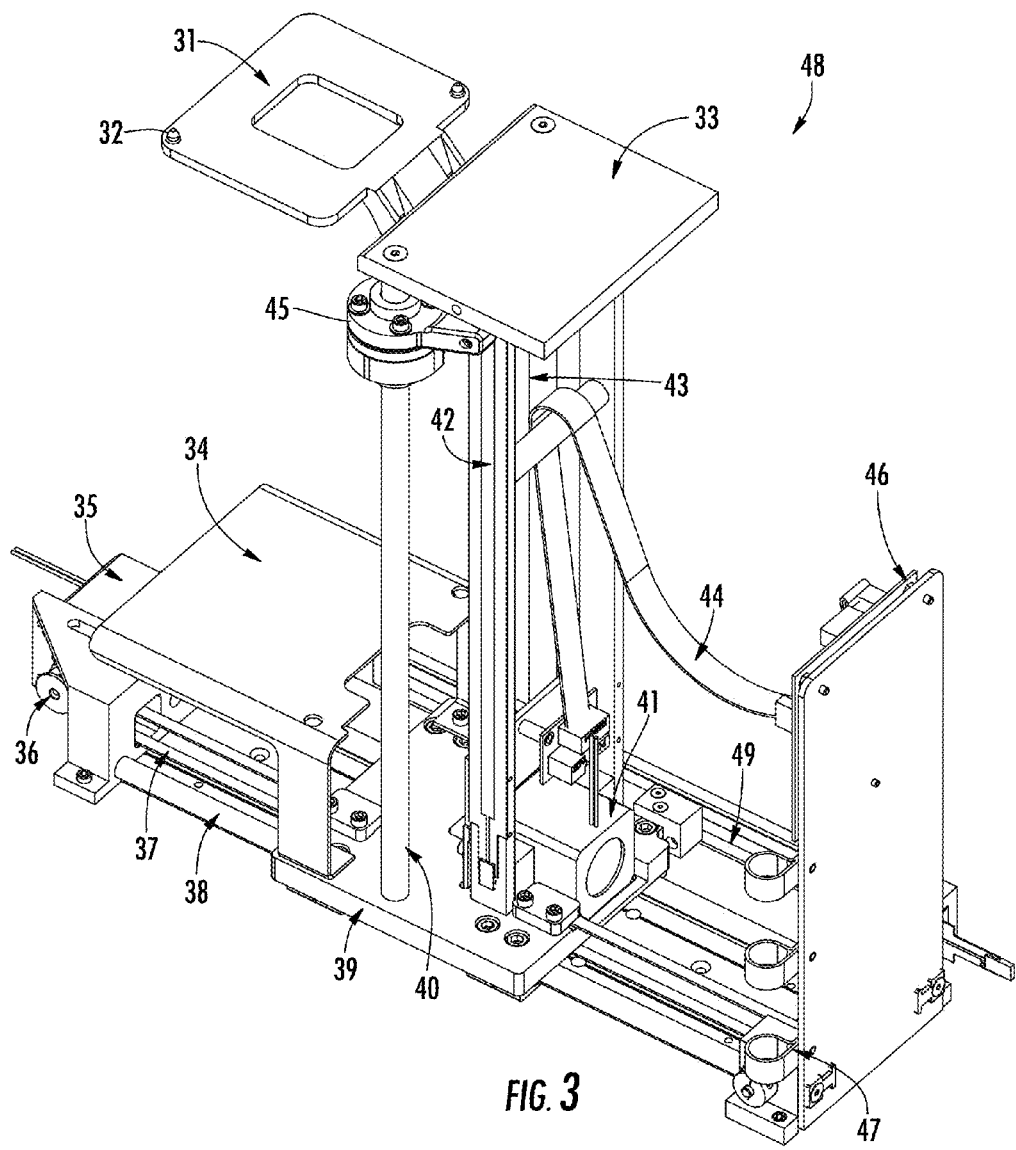
FIG. 3 shows the x-z stage assembly.
Figure 8:
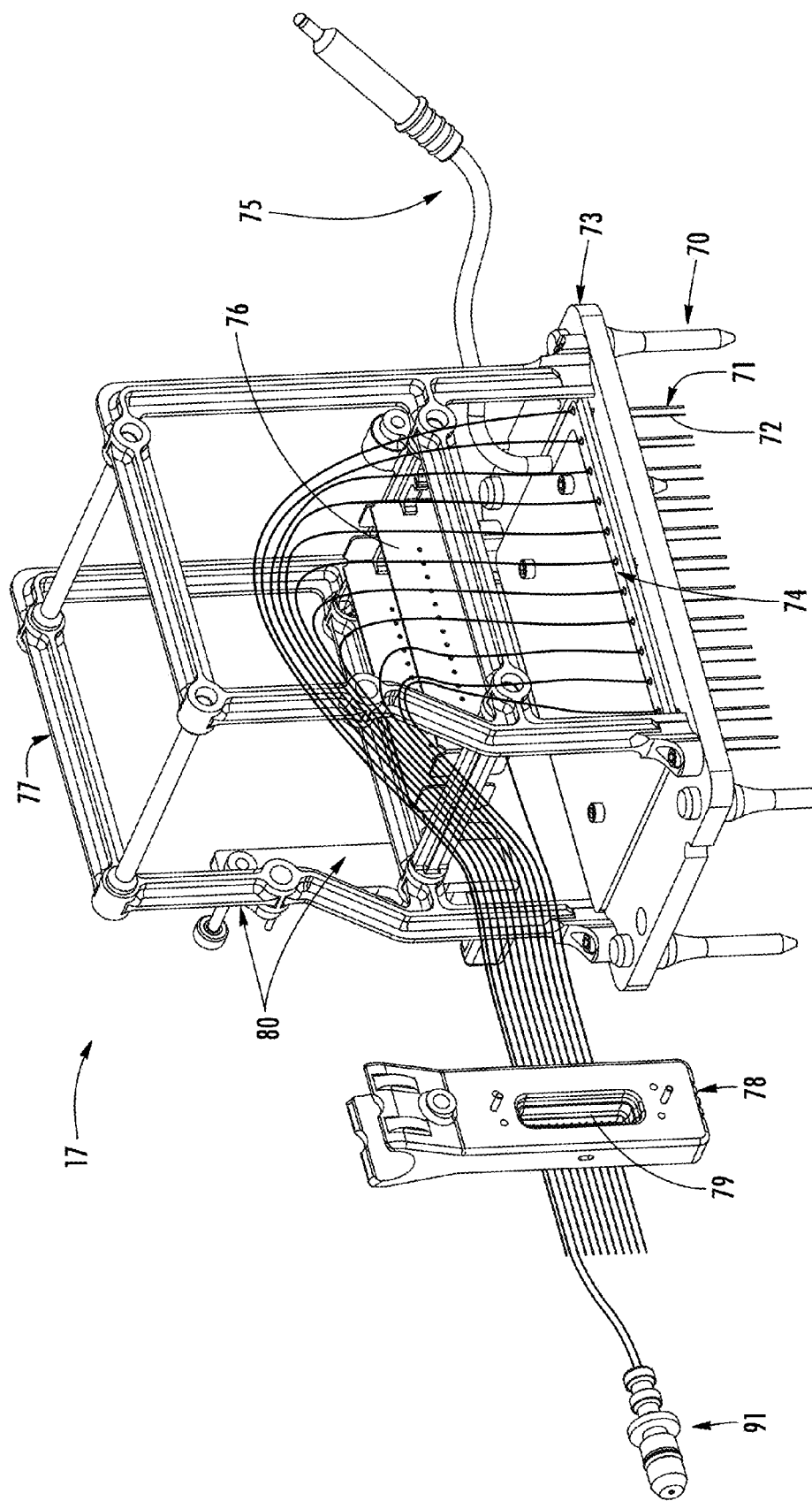
FIG. 8 shows a capillary array cartridge

FIG. 3 shows the x-z stage assembly 48, which is used to transport sample trays (50, FIG. 4) and associated tray holders (51, FIG. 4) from the drawers (12 FIG. 1) to the injection capillaries (72, FIG. 8) and injection electrodes (71, FIG. 8) of the capillary array (17, FIG. 8). The x-z stage assembly 48 is also used to position a buffer tray or waste tray (28, FIG. 2) from the drawers (11, FIG. 1) to the injection capillaries and electrodes of the capillary array (72, FIG. 8). The x-z stage assembly has a tray carrier 31 with alignment pins 32, which align with holes (57, FIG. 5) on the bottom of the tray holder (51, FIG. 4) to prevent subsequent sliding or movement of the tray holders during transport. A protective cover 34, made of metal or plastic, is used to prevent gels or other liquids from spilling onto the x-direction guide rails 38 and x-direction drive belt 37 of the stage assembly. An x-drive stepper motor 35 is used as the electro-mechanical driver for motion in the x-direction. A drive pulley 36 is attached to the stepper motor 35 and x-direction drive belt 37 which drives the stage carrier 39 back-and forth along the guide-bars 38. A second drive pulley (not shown) is used on belt 37 towards the back-end of the stage, which allows the belt to make a full loop when affixed to stage carrier 39. Any motor-induced movement of the belt induces a x-direction movement of the stage carrier 39 on the guide rails 38. A stepper-motor for the z-position is located at 41, which is attached to a drive pulley/belt configuration similar to that shown in the x-direction. The x-direction drive belt is shown as 43. The z-position motor/pulley/belt is used to move the tray carrier 31 up and down the guide bars 40. Top plate 33 serves as a structural support for the guide bars 40. An electrical communication strip 44 is used to communicate between an electrical motor control board 46 and the stepper motors 41 and 35. An x-direction membrane potentiometer strip 49, along with appropriate control electronics, is used to determine and control the absolute position of the stage carrier 39 in the x-direction. A z-direction membrane potentiometer strip 42, along with appropriate control electronics, is used to determine the absolute position of the tray carrier 31 in the z-direction. Linear encoders or rotational encoders (on the stepper motor) are alternative forms of positional measurement and control. Bearings 45 are located on each guide bar 40 and guide rail 38 to enable friction-free movement of both the tray carrier 31 and the stage carrier 39. Note that there are two guide bars or guide rails per axis. Electrical cord guide straps 47 are attached to a back support, which also holds the electrical control board 46 for the x-z stage assembly.

Figure 4:
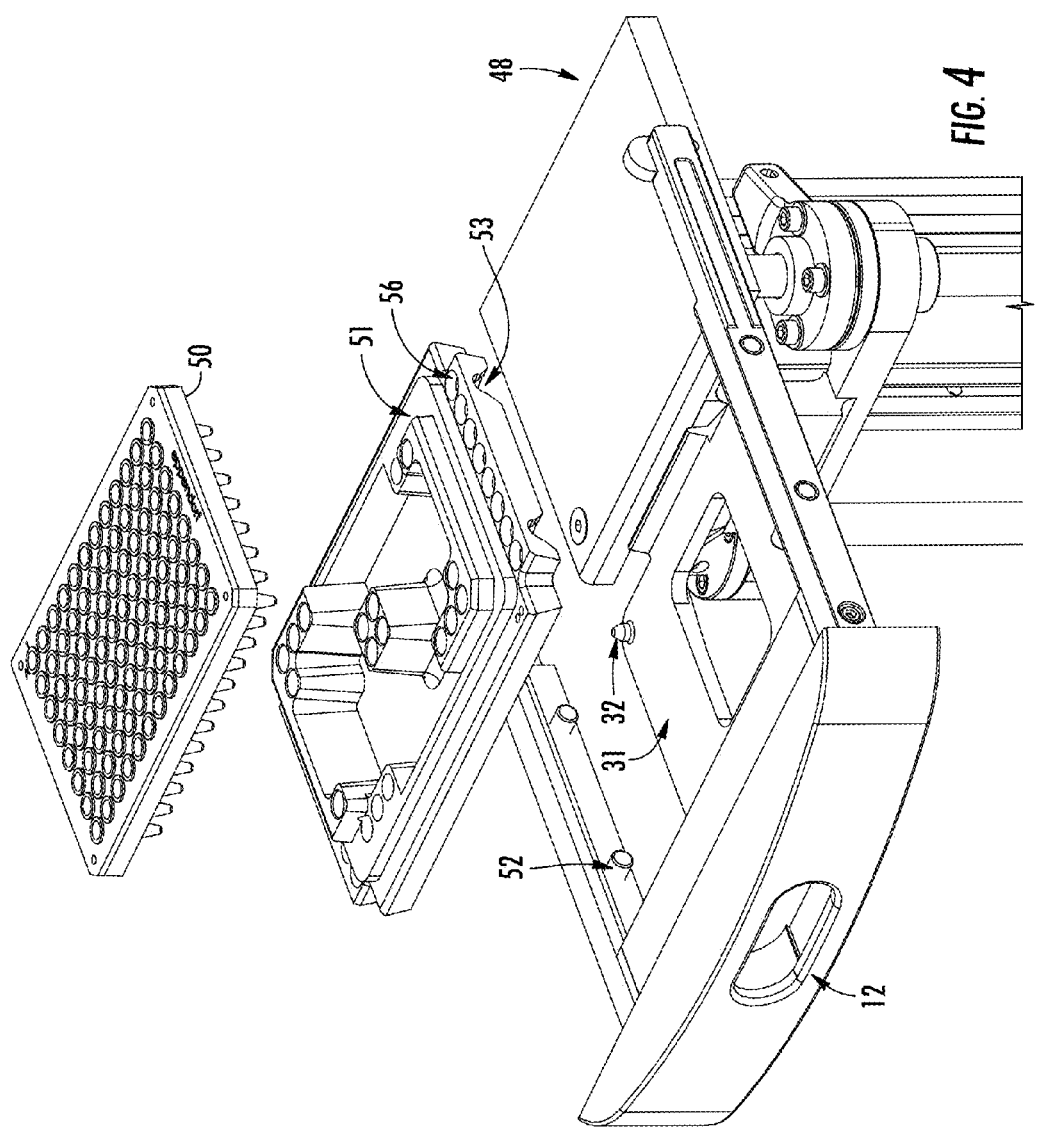
FIG. 4 shows a drawer, stage assembly, tray holder, and sample plate.
Figure 5:
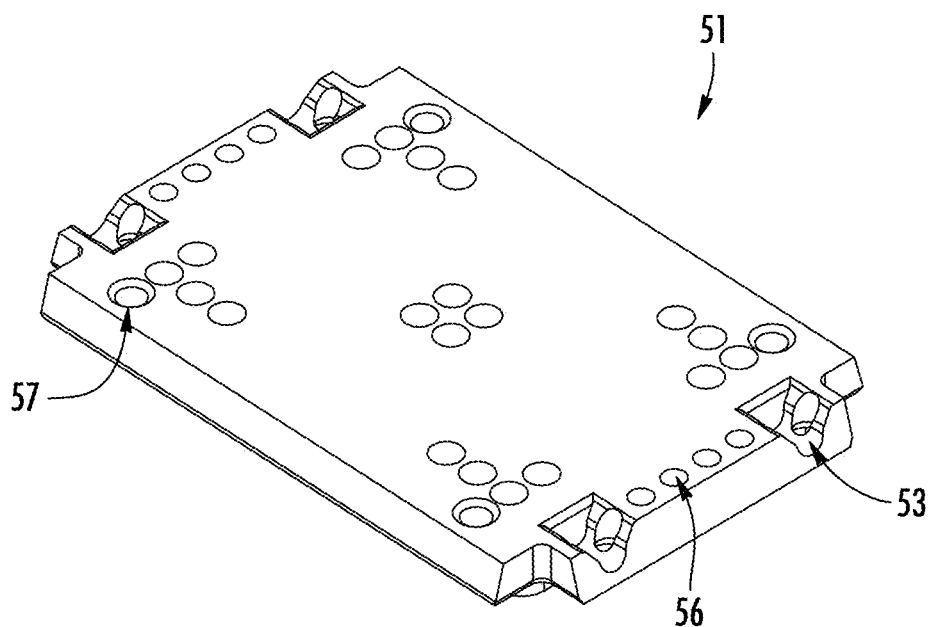
FIG. 5 shows the bottom of a tray holder.

FIG. 4 shows a drawer 12, superimposed on an image of the stage assembly 48, tray holder 51, and 96-well sample tray 50. The tray holder 51 is molded to specifically hold a 96-well plate, shown here as 50. Alternative moldings of the tray holder allow for different sample plates. Holes (57, FIG. 5) on the bottom of the tray holder 51 align with the alignment pins 32 of the tray carrier (31 FIG. 4). Notches 53 in the tray holder 51 align with alignment pins 52 on the drawer 12 to enable the tray holder to fit in a tight, reproducible way within the sample drawer.

Figure 6:
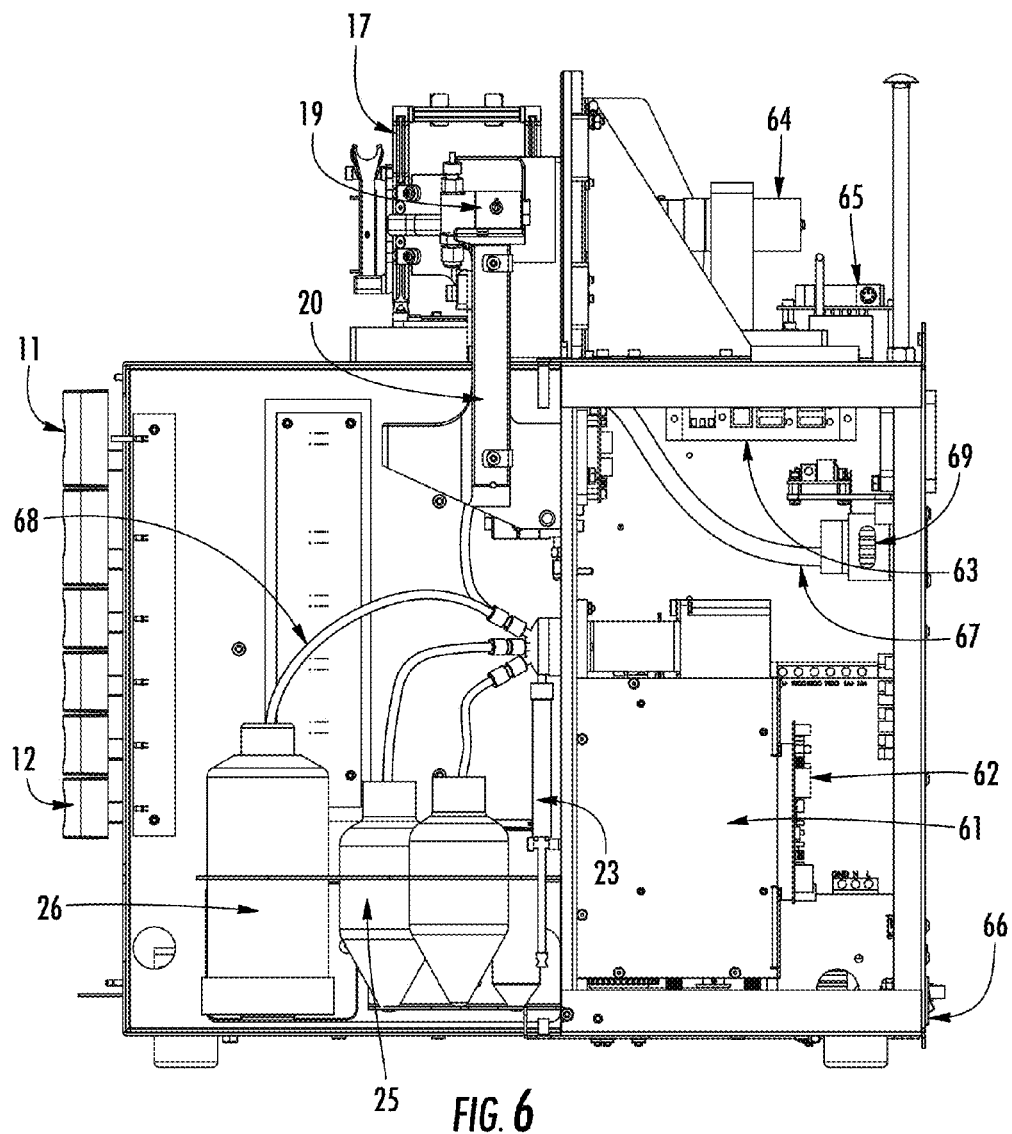
FIG. 6 shows a right-side view of the instrument without the cover.

FIG. 6 Shows a right side view of the electrophoresis system, with a chassis 66, pump motor and control system 61, pump control board 62, LED light engine 69, LED light line 67, high voltage power supply board 65, capable of applying 0.0 kV to 15 kV across the electrodes of the array, a CCD camera 64, capillary array cartridge 17, array window holder 19, reservoir 20, drawers 11, drawers 12, fluid lines 68, waste container 26, gel containers 25 and syringe 23. A USB electronic distribution bard is shown as 63.

Figure 7:
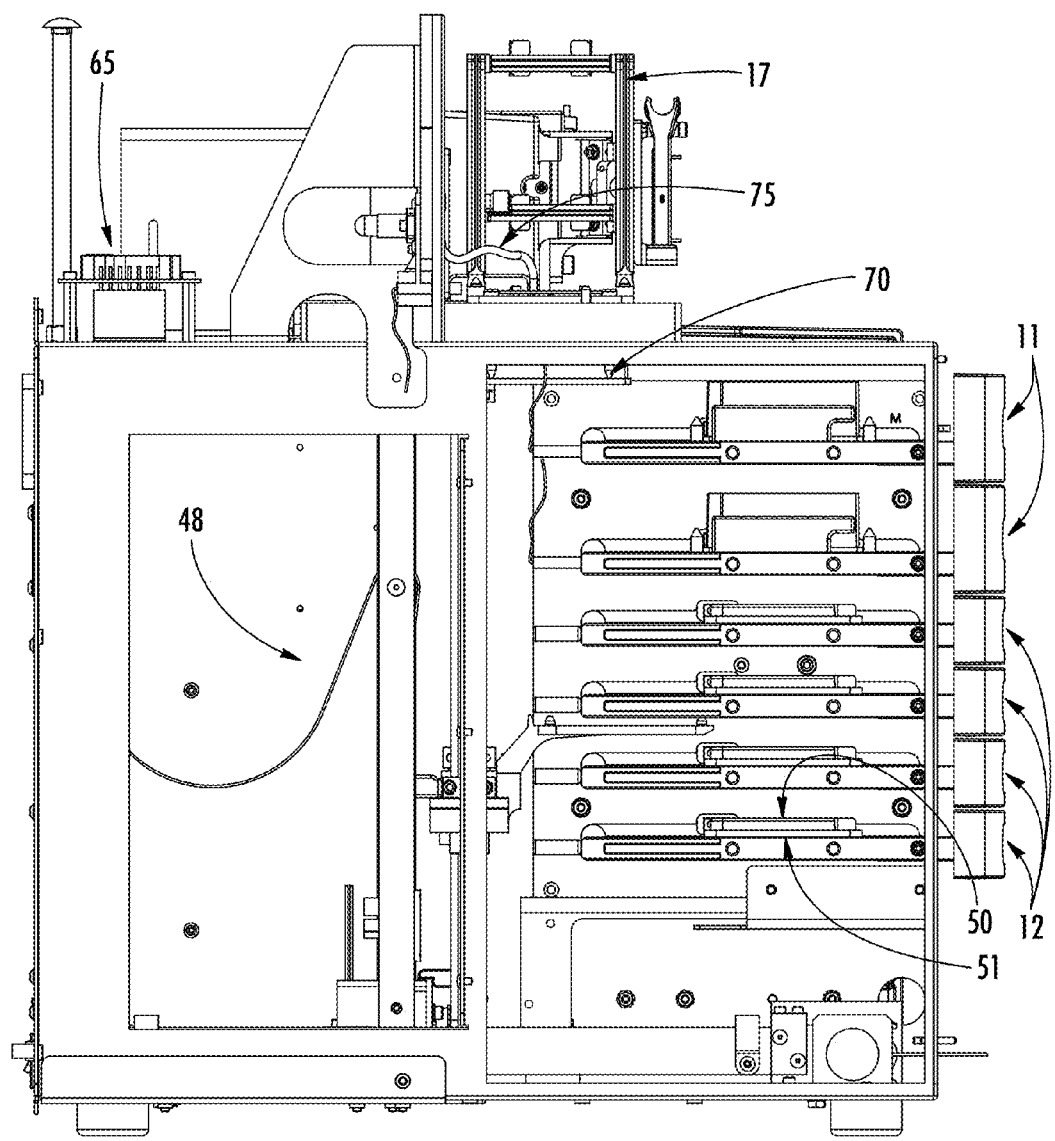
FIG. 7 shows the left-side view of the instrument without the cover.

FIG. 7 shows a left side-view of the electrophoresis unit showing the x-z stage assembly 48, which moves tray holders 51 and sample trays 50 from a drawer 12 or 11 to the bottom of array 17. The stage unit 48 can move the sample tray holder 51 and sample tray 50 up in the z-direction to lift the tray holder/sample tray off of the drawer, move back in the x-direction away from the sample drawers, and then move the sample plate up in the z-direction to the bottom of the capillary array 17. After electrokinetic or hydrodynamic injection, the stage unit 48 can move the sample tray holder/sample tray back down to the target drawer position (down in the z-direction), move forward in the x-direction just above the sample plate, and then drop down in the z-direction to set the sample tray holder/sample tray onto the drawer. When the sample tray holder 51 is resting in a drawer, the back edge of the sample tray holder 51 and sample tray 50 are aligned so that they do not lie directly underneath the array 17. This allows the sample stage tray carrier (31, FIG. 3) to move up and down along the entire z-axis with a tray holder/sample tray without colliding into other tray holders/sample trays in the drawers. The alignment pins (70, FIG. 8) on the bottom of array 17 are used to align the tray holder with a tray so that the capillary and electrode tips dip into each sample well of the sample plate and do not collide with other areas of the sample plate. This is shown in more detail in FIG. 11, which shows a sample tray holder 51 with a sample tray 50 aligned underneath a capillary array. Alignment holes 56 on the tray holder 51 force the alignment of the tray holder with the capillary array alignment pins 70.

FIG. 7 also shows high voltage power supply board 65 and high voltage power supply cable (to the array) 75.

FIG. 8 shows an array cartridge 17, with rigid plastic support structure 77, window storage and transport screw 80, capillary support cards 76, high voltage power supply cable 75, and insulating support structure 73 onto which the electric circuit board 74 is placed. Electrodes, 71 protrude through the electric circuit board 74, through the insulating support structure 73, and protrude through the bottom of the array. The electrode material is stainless steel or tungsten. The electrode dimension, which is not a critical aspect of the invention, is 50 mm diameter×29 mm length. The protrusion from the bottom of the cartridge base is 20.0 mm. The electrodes are soldered onto the circuit board 74. The high voltage power supply cable 75 is also soldered to the same circuit of the electrical circuit board, which enables contact of the electrodes 71 with the high voltage power supply (65, FIG. 6). Capillary tips 72 are threaded through the electric circuit board 74 and insulated support structure 73 and are aligned immediately adjacent and parallel to the electrode tips. The distance between the capillary tips and electrodes are from 0.1 mm to 4 mm. The ends of the capillaries and the ends of the electrode lie in a single plane (i.e. the capillary tips and electrode tips are the substantially the same length, with length variation of no more than about +/−1 mm. Preferably, the length variation of capillary tips and electrode tips is less than 0.5 mm. The capillaries thread through the bottom of the capillary array, through the insulating support structure 73, through the electric circuit board 74, through the capillary support cards 76 (which are supported by the rigid plastic support structure 77) through the capillary window holder 70 with capillary windows 79 centered in the opening of the window holder, and then finally through the capillary reservoir tip 91, in which all capillaries (in this case 12) are threaded through a single hole. For 96 capillary arrays, capillaries are threaded in groups of 12 in the capillary reservoir tip 79. The capillaries are held in place in the reservoir tip 91 with an adhesive, such as a thermally or uv-curable epoxy.

Figure 12A:
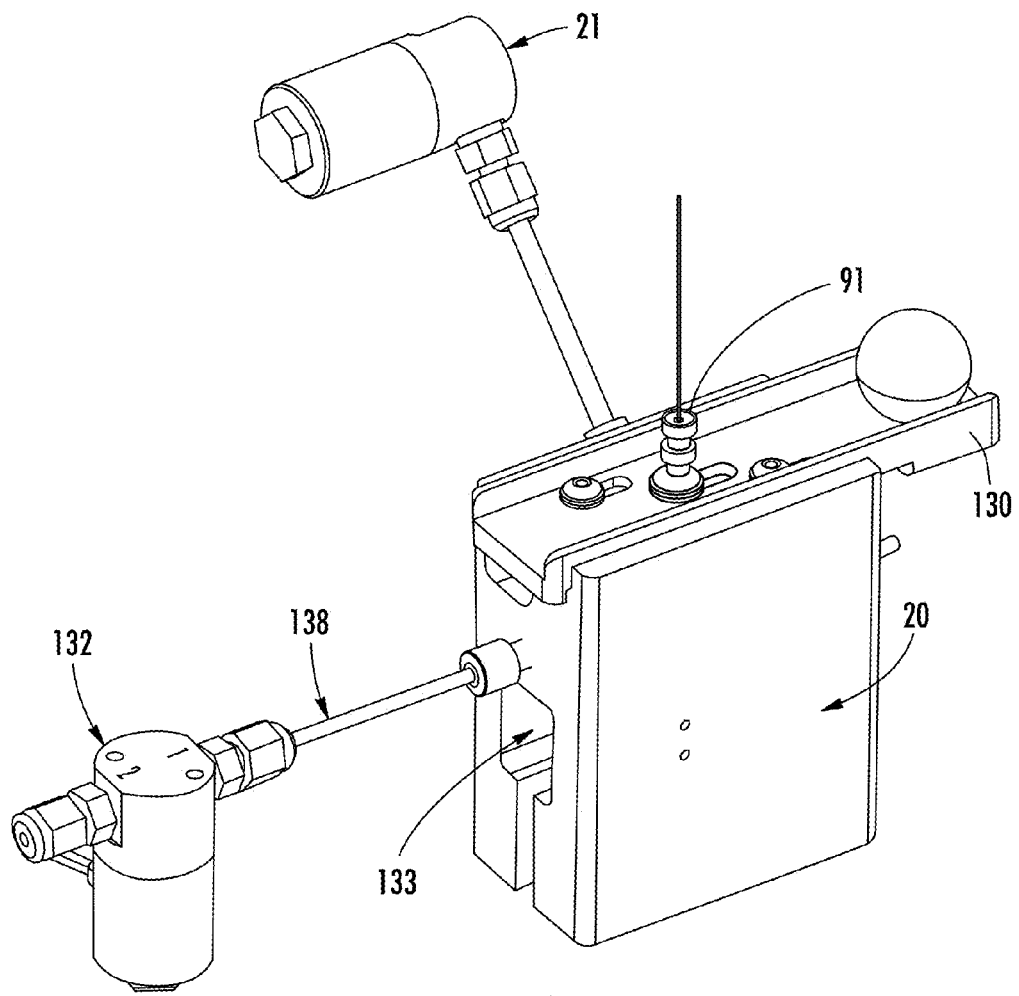
FIG. 12A shows a view of the capillary electrophoresis reservoir system.

FIG. 12A shows the reservoir, with reservoir body 20, capillary reservoir tip 91, slider bar 130 (for locking capillary reservoir tip into the reservoir, through alignment of a notch on the capillary reservoir tip 91 and the slider bar 130), vent block valve 21, waste tube out 138, waste block valve 132, and pressure transducer cavity 133.

Figure 12B:
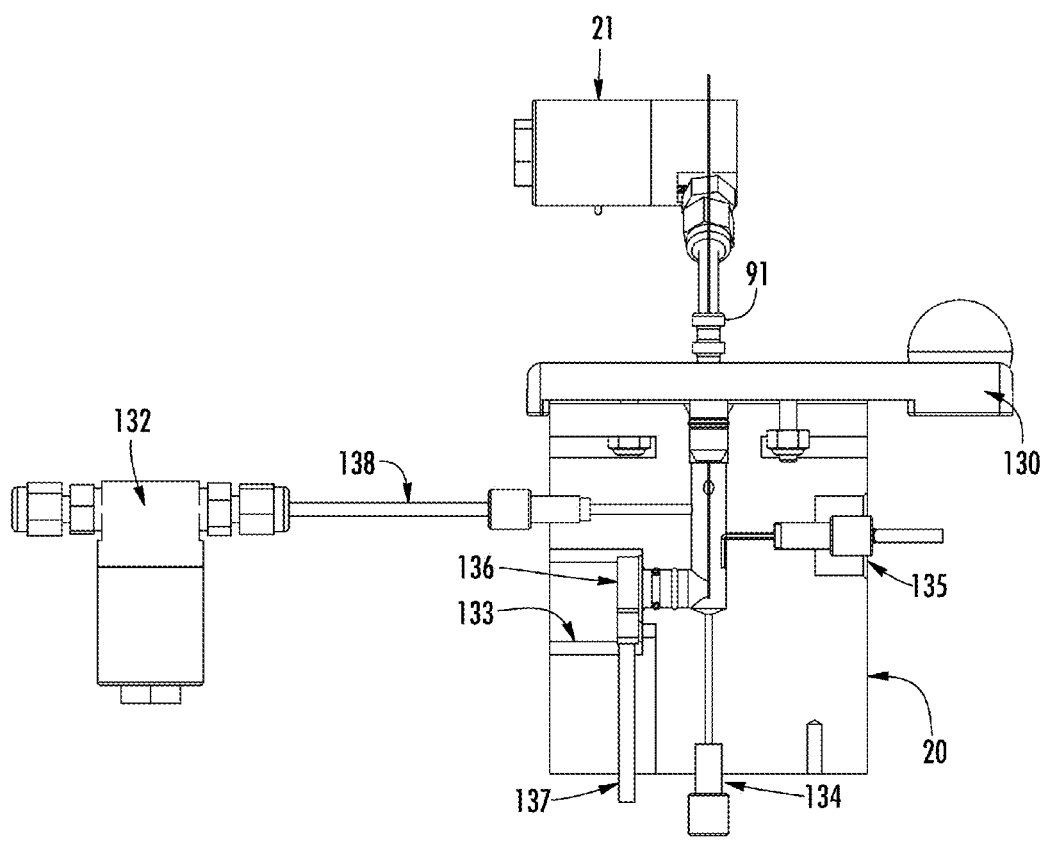
FIG. 12B shows a view of the capillary electrophoresis reservoir system.

FIG. 12B shows an alternate cut-out view of the reservoir, with reservoir body 20, capillary reservoir tip 91, slider bar 130, vent block valve 21, waste tube out 138, waste block valve 132, electrode for attachment to ground 135, pressure transducer cavity 133, pressure transducer 136, pressure transducer cable for attachment to analog/digital board 137, and fluid tube input 134 (from syringe pump 23 FIG. 2).

The reservoir body can be made of any solid material such as acrylic, Teflon, PETE, aluminum, polyethylene, ABS, or other common metals or plastics. The key criterion is that the material is durable and chemically resistant to the materials used. A preferred material is acrylic or Teflon.

Figure 11:
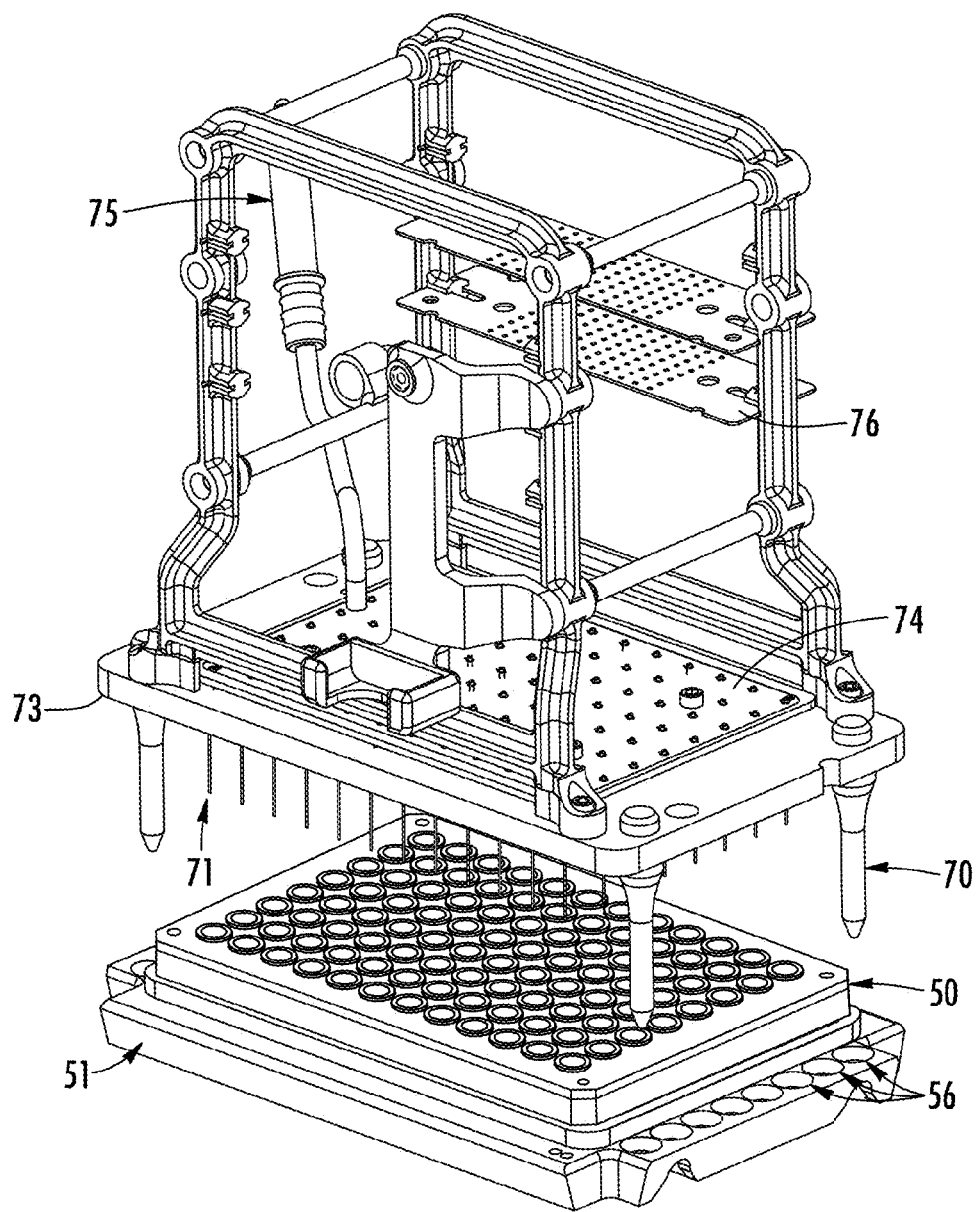
FIG. 11 shows the positioning of a sample plate under the array by the stage.
Figure 13A:
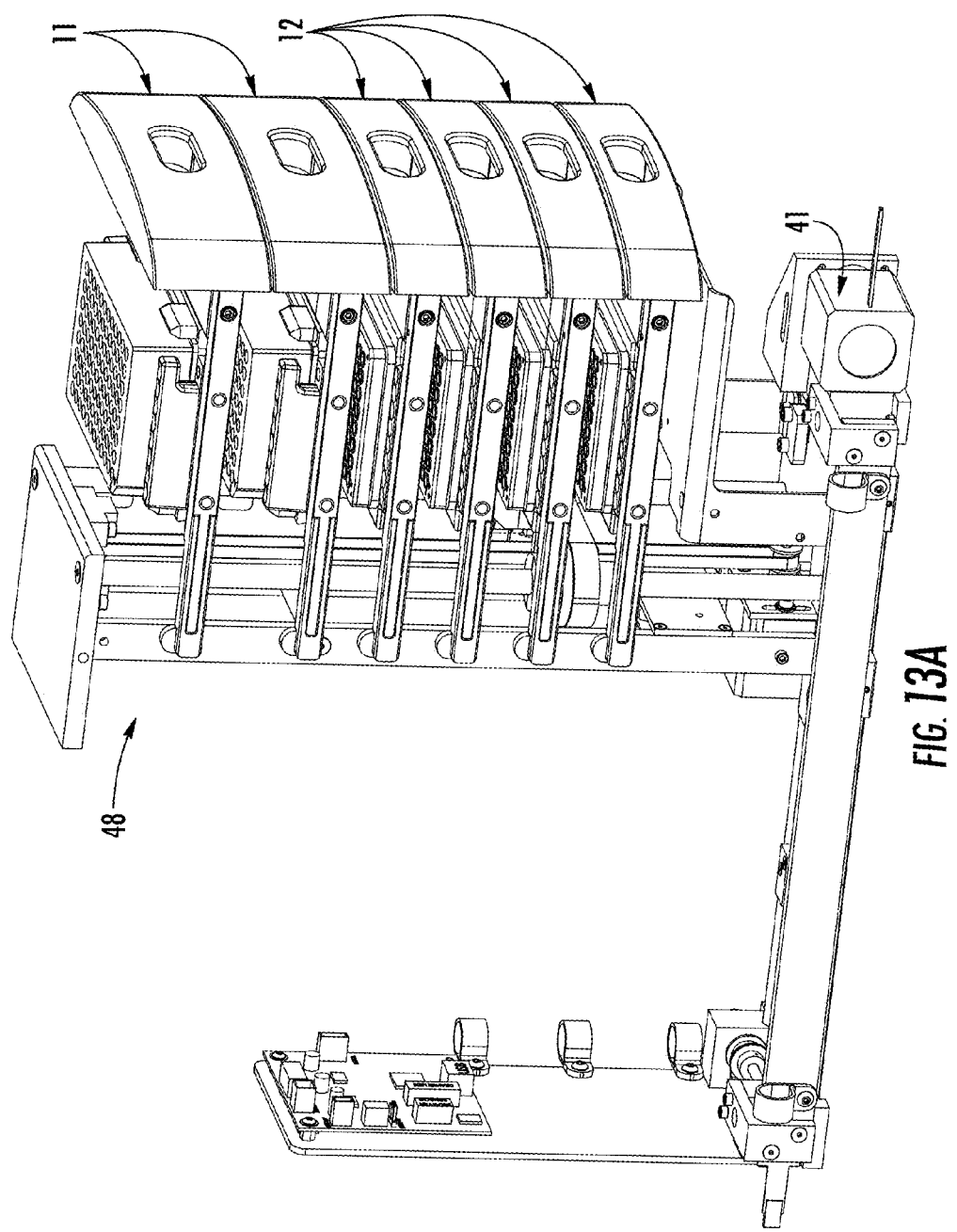
FIG. 13A shows a view of the x-z stage relative to the drawers.
Figure 13B:
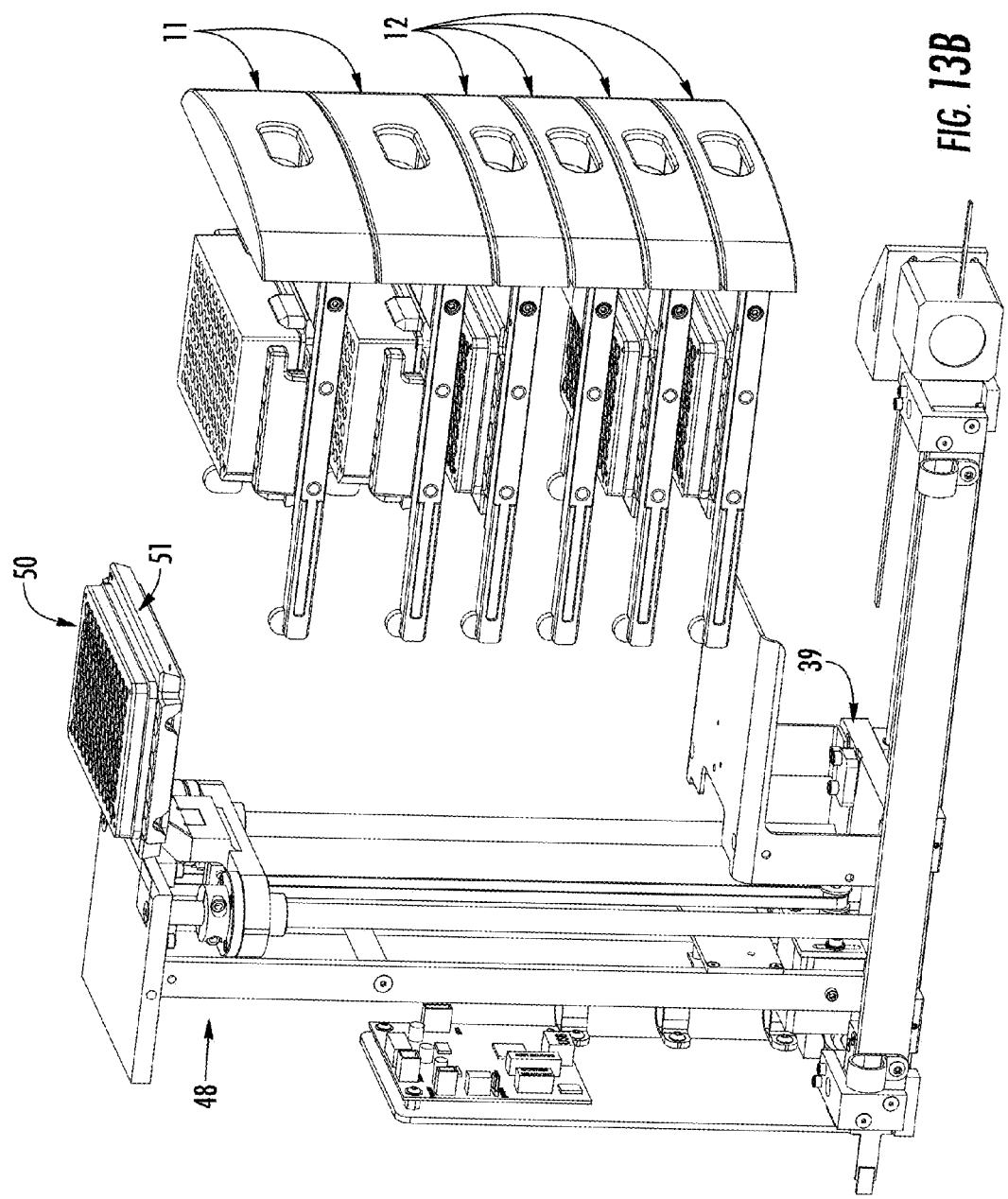
FIG. 13B shows a view of the x-z stage with a sample tray lifted.

FIG. 13A shows the x-z stage unit 48 in relation to the drawers 11 and 12. The x-z stage is located directly behind the drawers, and can move the stage carrier (39, FIG. 13B) back- and forth in the x-direction using the stepper-motor for the z-position 41. A sample tray is removed from a drawer by first moving the stage forward, towards the drawers, in the x-direction. The tray carrier (31, FIG. 3) lifts a tray holder up and off a drawer in the z-direction using the z-direction stepper motor (41, FIG. 3). The stage carrier is then moved back in the x-direction, away from the drawers, as shown in FIG. 13B. The stage carrier 39 is then moved up in the z-direction to move the tray holder 51 and sample tray 50 to the injection position of the capillary array (FIG. 11).

A typical strategy for pumping fluids for capillary electrophoresis is as follows. Consider the following 6 positions of the six-way distribution valve (29, FIG. 2) on the syringe. Position 1 is connected to the bottom of the reservoir (134, FIG. 12B); position 2 is connected through a tube to a bottle of conditioning fluid (a fluid for conditioning the walls of the capillaries); position 3 is connected to a "Gel 1" which is used for the analysis of genomic DNA, position 4 is connected to a "Gel 2" which is used for the analysis of fragmented DNA, position 5 is unused, and position 6 is connected to the waste bottle.

Step A: The reservoir is first emptied by opening position 1 (reservoir), filling the syringe with fluid that is in the reservoir, closing position 1, opening position 6, and emptying fluid to the waste. This is repeated until the reservoir is empty. Block valves 21 and 132 are kept open during this process to enable efficient draining of the reservoir.

Step B: The reservoir is then filled with conditioning solution by opening position 2, filling the syringe with conditioning solution, closing position 2, opening position 1, and filling the reservoir with conditioning solution. Block valve 21 is closed, but block valve 132 to waste is open, enabling the over-filling of the reservoir with conditioning solution.

Step C: The capillaries are filled by closing both vent block valve 21 and waste vent valve 132. The syringe is filled with capillary conditioning solution. Position 1 is opened, and fluid is pressure filled through the capillaries at a minimum of 100 psi for a pre-determined time, which may range from 1 minute to 20 minutes.

Step D: The reservoir is emptied by step A, and then re-filled with gel using the same process as in Step B, except that position 3 for the gel is used on the 6-way distribution valve.

Step E: The capillaries are filled with gel using a process analogous to Step C.

After steps A-E, the capillaries are ready for electrophoresis.

A general strategy and process for analyzing samples using electrophoresis is as follows.

Samples are placed into a 96-well plate for analysis. The user places the sample plate into a sample drawer (12, FIG. 1), and then adds jobs to a computer-based queue, corresponding to the analysis of a specific row or the entire sample plate in the drawer. The computer, which is the control system of the instrument, executes the analysis of the row or entire tray of interest.

A key embodiment of the invention is the workflow of the capillary electrophoresis system. Drawers (11, FIG. 1) allow easy placement of buffer and waste trays into the system. Drawers (12, FIG. 1) allow easy placement of sample trays into the system. Of particular importance is the ability to place or remove sample trays from drawers (12, FIG. 1) while the system is performing capillary electrophoresis. Indicator lights (120, FIG. 1) show if a tray is present or absent in a drawer, which let users know if a drawer is in place. A typical workflow for a 12-capillary multiplex system is as follows: User A walks up to the machine with sample tray 1, and places it into the third drawer from the top (one of drawers 11, FIG. 1). User "A" then fills a queue with three jobs, which correspond to performing capillary electrophoresis on the three rows of samples: sample tray 1 row A, sample tray 1 row B, and sample tray 1 row C. User "A" then instructs the computer to execute the queue, and as a result, the system begins capillary electrophoresis of sample tray 1, row A, and will continue executing jobs in the queue until there are no more jobs. User "B" then comes up and places sample tray 2 into the fourth drawer from the top (one of drawers 11, FIG. 1). User "B" then adds 8 jobs to the queue corresponding the performing of capillary electrophoresis on 8 rows of samples: sample tray 2, rows A-H. The computer will continue analyzing user "A" samples until they are finished, and then continue on with the analysis of user "B" samples. In the meantime, user "C" walks up and loads sample tray 3 into the fifth drawer from the top (one of drawers 11, FIG. 1). User "C" then adds 1 job to the queue corresponding to the analysis of 1 row of samples: sample tray 3, row A. This process can continue indefinitely, as long as there is sufficient gel in gel containers (25 in FIG. 2), or if there is sufficient run buffer in the buffer tray (28, FIG. 2) located in top drawer 11, FIG. 1. It is, among other things, the enabling of this workflow, via the drawers sample stage, and computer program with a queue for loading jobs that differentiates the present invention from the prior art systems for CE workflow.

An important embodiment of the present invention is a computer program that enables users to load a sample plate into the desired vertical drawer (12, FIG. 1), and instruct the system to run the desired rows or entire sample plate, while the system is running other samples. This allows multiple users to load samples and/or sample plates, or a single user to load multiple samples and/or sample plates without first having to wait for the electrophoresis of other samples to be complete.

Figure 9:
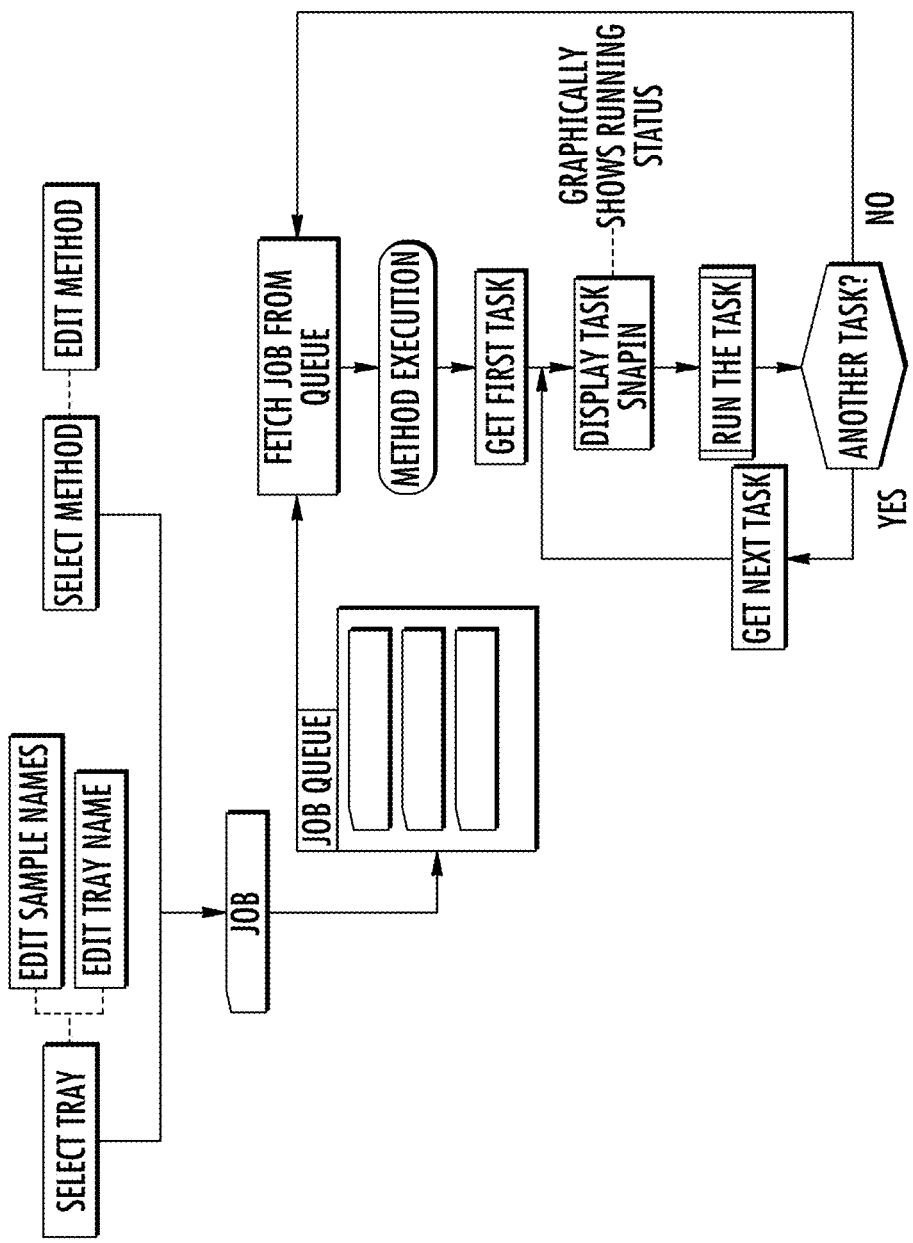
FIG. 9 shows the flow-chart for the software control program for creating a queue of jobs.

FIG. 9 shows the general flow diagram of the work process and computer program. A user loads a sample tray into a drawer (12, FIG. 1) of the system. On the computer, user then selects the tray, edits sample names and/or tray name. User further selects or defines a method (time of separation, electric field used for separation, gel selection, etc.). This selected tray, along with an associated method is defined as a "job", which is then placed into a queue. The computer as an instrument control device, fetches jobs from the queue, and controls the instrument for every task, including operation of the syringe pump, operation of the high voltage power supply, and the motion control stage (48, FIG. 3). For each run (or job), there may be a variety of tasks, with each task requiring direct command and control of subunits of the system. Tasks associated with control of the syringe pump include empty-ing/filling the reservoir with conditioning fluid, forcing conditioning fluid through the capillaries, emptying/filling the reservoir with gel, forcing gel through the capillaries. Tasks associated with control of the x-z stage may include moving or removing a waste tray to/from the inlet capillaries and electrodes of the capillary array, moving or removing a buffer tray to/from the inlet capillaries and electrodes of the capillary array, or moving/removing a sample tray to/from the inlet capillaries and electrodes of the capillary array. Tasks associated with control of the high voltage power supply include turning off/on a high voltage for capillary electrophoresis separation. Other tasks are associated with the camera (acquisition of data), and block valves. For each set of samples, the program will complete all tasks required to obtain a set of electropherograms. Once these tasks are complete, the program fetches another job from the queue. If the queue is empty, all sample runs are complete (until the user initiates another queue).

Figure 10:
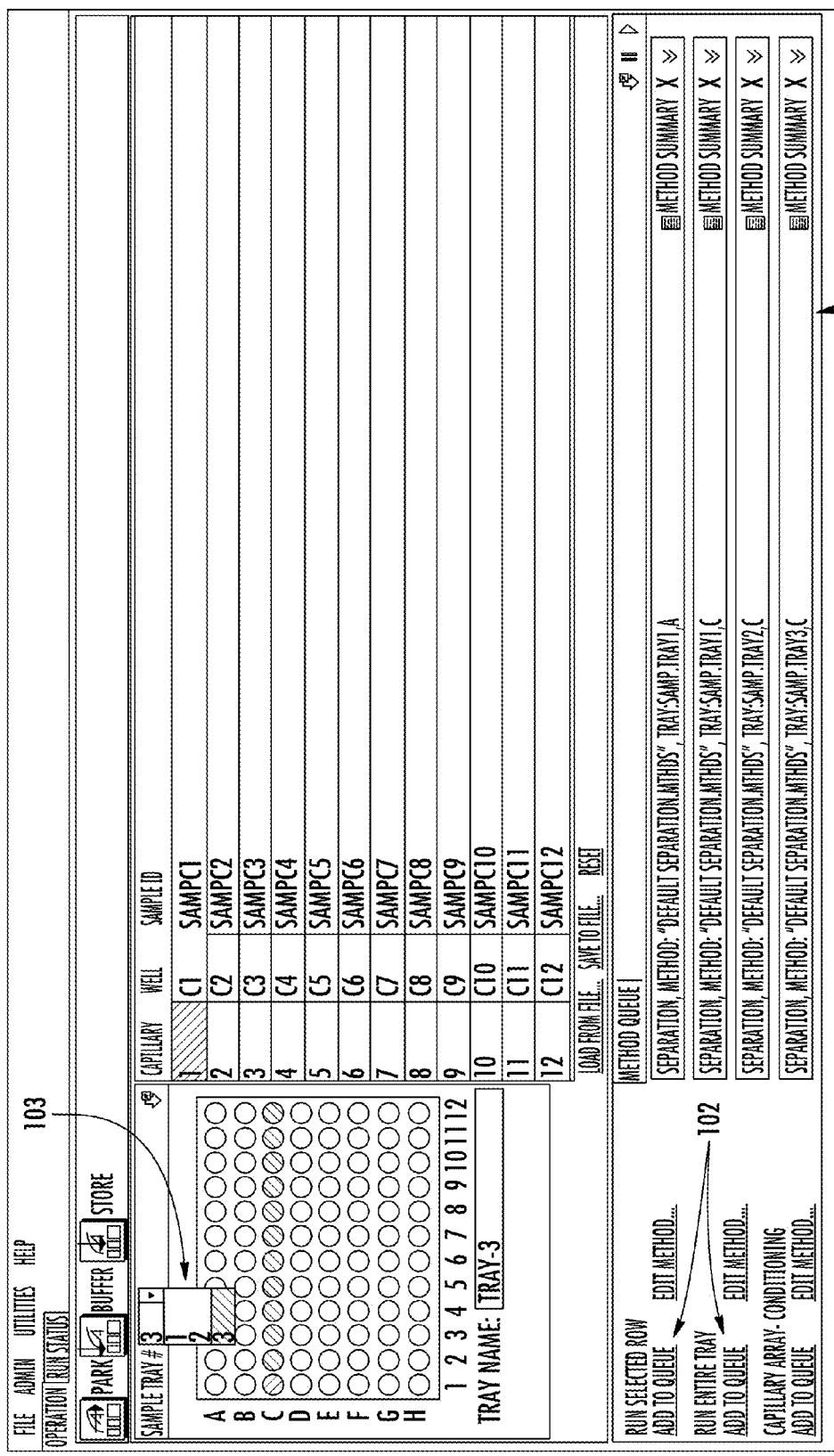
FIG. 10 shows a computer screen image of the computer software.

The graphical result of this computer program is shown in FIG. 10, which shows a list of samples to be analyzed in queue 101, an option to add rows or trays to the queue 102, and an option to select the tray number for analysis 103. It is these three aspects that are critical to software portion of the invention: a) Selection of tray 103 (corresponding to a drawer 11 FIG. 1) b) Adding the sample set to a queue (102, FIG. 10) and c) A queue of active samples for analysis (101, FIG. 10), which are executed in sequence until all jobs are complete. Another critical aspect is the ability to add samples to instrument drawers (11, FIG. 1) and queue (101, FIG. 10) while the instrument is running other samples.

As can be seen from the above description, the system eliminates the need for expensive robots, enables the user to run many samples per day, allows loading of new samples while running others, and yet has a small size footprint.

What is claimed is:

1. An electrophoresis console to enhance workflow, comprising:
    a console housing an operable multiplex capillary electrophoresis system;
    a plurality of externally accessible drawers for holding sample plates or buffer plates in said console; and
    an x-z mechanical stage motion control system having an x direction membrane potentiometer for absolute position control and a z direction membrane potentiometer for absolute position control built within said console to move said sample plates or buffer plates back and forth and up and down from any one of said drawers to an injection position of said capillary electrophoresis system and back.

2. The apparatus of claim 1 which includes as the externally accessible drawers at least four vertically stacked drawers.

3. The electrophoresis apparatus according to claim 1 which includes as the externally accessible drawers at least six vertically stacked drawers.

4. The electrophoresis console of claim 1, wherein samples can be placed into at least some of said drawers while the console is running and collecting electrophoresis data.

5. The electrophoresis console of claim 1, which includes in it an operative computer program that enables multiple users to load multiple samples into said drawers, and to run said multiple samples sequentially while the system is performing electrophoresis.

6. The electrophoresis console of claim 2 wherein the x-z mechanical stage motion control system includes:
    a sample loader to load samples into sample plates located in said vertically stacked drawers; and
    a sample transporter.

7. The electrophoresis console of claim 6, further comprising a computer controller that enables users to load a sample plate into the sample loader and to instruct the system to run the samples, while the system is running other samples.

8. In an electrophoresis console which includes within it:
    a capillary array with a plurality of capillaries that can be filled with an electrophoresis medium; and
    a fluid handling system for injecting said capillaries with said electrophoresis medium or other fluids, the improvement comprising:
        (a) a plurality of externally accessible vertically stacked drawers for holding sample plates or buffer plates in said electrophoresis console; and
        (b) an x-z mechanical stage motion control system having an x direction membrane potentiometer for absolute control and a z direction membrane potentiometer for absolute position control built into the console that moves said sample plates or said buffer plates from any one of said drawers to an injection position of said capillary array and back.

9. The console of claim 1 wherein the electrophoresis system includes LED indicator lights to indicate presence or absence of buffer plates or sample plates.

10. The console of claim 8 wherein the electrophoresis system includes LEI) indicator lights to indicate the presence or absence of buffer plates or sample plates.

* * * * *